(12) United States Patent
Luzader et al.

(10) Patent No.: US 11,717,453 B2
(45) Date of Patent: *Aug. 8, 2023

(54) ABSORBENT ARTICLE HAVING A PRINTED REGION

(71) Applicant: The Procter & Gamble Company, Cincinnati, OH (US)

(72) Inventors: Christine Gail Luzader, Loveland, OH (US); Michael Philip Krell, Cincinnati, OH (US); Maria Fernanda Páez, Edo. Miranda (VE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/190,492

(22) Filed: Mar. 3, 2021

(65) Prior Publication Data

US 2021/0186774 A1    Jun. 24, 2021

Related U.S. Application Data

(60) Continuation of application No. 15/679,618, filed on Aug. 17, 2017, now Pat. No. 10,959,888, which is a division of application No. 13/974,511, filed on Aug. 23, 2013, now abandoned.

(51) Int. Cl.
*A61F 13/475* (2006.01)
*A61F 13/513* (2006.01)
*A61F 13/476* (2006.01)
*A61F 13/537* (2006.01)

(52) U.S. Cl.
CPC ........ *A61F 13/4758* (2013.01); *A61F 13/476* (2013.01); *A61F 13/51394* (2013.01); *A61F 13/53747* (2013.01)

(58) Field of Classification Search
CPC ................ A61F 13/4758; A61F 13/476; A61F 13/51394; A61F 2013/51078; A61F 2013/5683; A61F 13/5605
See application file for complete search history.

(56) References Cited

U.S. PATENT DOCUMENTS

| | | |
|---|---|---|
| 2,881,761 A | 4/1959 | Kenner |
| 4,548,603 A | 10/1985 | Ichijo |
| 4,623,340 A | 11/1986 | Luceri |
| 4,673,403 A | 6/1987 | Serbiak et al. |
| 4,908,026 A | 3/1990 | Becker et al. |
| 4,909,879 A | 3/1990 | Ball |

(Continued)

FOREIGN PATENT DOCUMENTS

| | | |
|---|---|---|
| CN | 101999964 A | 4/2011 |
| CN | 301926021 | 5/2012 |

(Continued)

OTHER PUBLICATIONS

PCT Search Report and Written Opinion for PCT/US2014/050677 dated Nov. 14, 2014.

(Continued)

*Primary Examiner* — Michele M Kidwell
(74) *Attorney, Agent, or Firm* — Wiliam E. Gallagher; George H. Leal

(57) ABSTRACT

Asymmetrical absorbent articles having printed regions to facilitate individual placement of the absorbent article are described.

14 Claims, 6 Drawing Sheets

(56) References Cited

U.S. PATENT DOCUMENTS

| | | |
|---|---|---|
| 4,950,264 A | 8/1990 | Osborn, III |
| 5,006,394 A | 4/1991 | Baird |
| 5,009,653 A | 4/1991 | Osborn, III |
| 5,188,625 A | 2/1993 | Van Iten et al. |
| 5,261,899 A | 11/1993 | Visscher et al. |
| H1376 H | 11/1994 | Osborn, III |
| 5,389,094 A | 2/1995 | Lavash et al. |
| 5,401,267 A | 3/1995 | Couture-dorschner et al. |
| 5,437,653 A | 8/1995 | Gilman et al. |
| 5,439,458 A | 8/1995 | Noel |
| 5,454,800 A | 10/1995 | Hirt et al. |
| 5,458,590 A | 10/1995 | Schleinz et al. |
| 5,503,076 A | 4/1996 | Yeo |
| 5,558,663 A | 9/1996 | Weinberger et al. |
| 5,562,037 A | 10/1996 | Schleinz et al. |
| 5,566,616 A | 10/1996 | Schleinz et al. |
| 5,675,079 A | 10/1997 | Gilman et al. |
| 5,683,752 A | 11/1997 | Coenen et al. |
| 5,713,886 A * | 2/1998 | Sturino ............... A61F 13/5616 604/385.04 |
| 5,766,389 A | 6/1998 | Brandon et al. |
| 5,795,345 A | 8/1998 | Mizutani et al. |
| 5,817,079 A | 10/1998 | Bergquist et al. |
| 5,818,719 A | 10/1998 | Brandon |
| 5,897,541 A | 4/1999 | Uitenbroek et al. |
| 6,074,376 A | 6/2000 | Mills |
| 6,075,178 A | 6/2000 | La |
| 6,231,555 B1 | 5/2001 | Lynard |
| 6,264,640 B1 | 7/2001 | Sutton |
| 6,297,424 B1 | 10/2001 | Olson |
| 6,482,192 B2 | 11/2002 | Haarer |
| 6,569,136 B1 | 5/2003 | Tao |
| 6,595,042 B2 | 7/2003 | Holliday et al. |
| 6,695,697 B1 | 2/2004 | Okada |
| 6,946,585 B2 | 9/2005 | London |
| 6,949,689 B2 | 9/2005 | Noda |
| 7,163,528 B2 | 1/2007 | Christon |
| 7,241,280 B2 | 7/2007 | Christon et al. |
| 7,270,651 B2 | 9/2007 | Adams |
| 7,306,582 B2 | 12/2007 | Adams |
| 7,311,696 B2 | 12/2007 | Christon et al. |
| 7,537,585 B2 | 5/2009 | Christon et al. |
| 7,959,620 B2 | 6/2011 | Miura et al. |
| 8,314,285 B2 | 11/2012 | Veglio et al. |
| 10,959,888 B2 * | 3/2021 | Luzader ............ A61F 13/51394 |
| 11,058,591 B2 * | 7/2021 | Vohwinkel ........ A61F 13/47245 |
| 2001/0031954 A1 | 10/2001 | Jordan |
| 2002/0017354 A1 | 2/2002 | Riddell |
| 2003/0065299 A1 | 4/2003 | Carlucci |
| 2003/0109839 A1 | 6/2003 | Costea |
| 2003/0114809 A1 | 6/2003 | Gagliardi |
| 2003/0114811 A1 | 6/2003 | Christon |
| 2003/0114818 A1 | 6/2003 | Benecke |
| 2003/0135174 A1 | 7/2003 | Benecke et al. |
| 2003/0207091 A1 | 11/2003 | Nair |
| 2004/0015145 A1 | 1/2004 | Miura |
| 2004/0127875 A1 | 7/2004 | Hammons et al. |
| 2004/0138636 A1 * | 7/2004 | Cardin ............... A61F 13/47245 604/385.04 |
| 2004/0170813 A1 | 9/2004 | Digiacomantonio |
| 2004/0243087 A1 | 12/2004 | Kinoshita et al. |
| 2005/0124959 A1 * | 6/2005 | Alcantara ............ A61F 13/476 604/385.04 |
| 2006/0116652 A1 * | 6/2006 | Miura ..................... A61F 13/47 604/385.101 |
| 2006/0129114 A1 | 6/2006 | Mason et al. |
| 2006/0129116 A1 | 6/2006 | Hughes et al. |
| 2008/0255529 A1 | 10/2008 | Christon et al. |
| 2008/0255530 A1 | 10/2008 | Christon et al. |
| 2008/0262454 A1 | 10/2008 | Christon et al. |
| 2011/0202027 A1 | 8/2011 | Christon et al. |
| 2011/0270208 A1 | 11/2011 | Miura et al. |
| 2012/0253308 A1 | 10/2012 | Misiti et al. |
| 2012/0310200 A1 | 12/2012 | Christon et al. |
| 2013/0123731 A1 | 5/2013 | Mercer |
| 2013/0165885 A1 | 6/2013 | Kurihara |
| 2015/0057632 A1 | 2/2015 | Luzader et al. |

FOREIGN PATENT DOCUMENTS

| | | |
|---|---|---|
| CN | 202821865 U | 3/2013 |
| EP | 0605730 A1 | 7/1994 |
| EP | 0774946 B1 | 5/1997 |
| EP | 0794280 A2 | 9/1997 |
| EP | 0934737 A1 | 8/1999 |
| EP | 0951889 A1 | 10/1999 |
| EP | 1057465 A1 | 12/2000 |
| EP | 1199057 A1 | 4/2002 |
| EP | 1203571 A2 | 5/2002 |
| EP | 1295711 A1 | 3/2003 |
| GB | 1070514 A | 6/1967 |
| GB | 2354449 A | 3/2001 |
| JP | 59190229 | 12/1984 |
| JP | H0788128 A | 4/1995 |
| JP | 3021237 U | 8/1995 |
| JP | 2003199786 A | 7/2003 |
| WO | 9119471 A1 | 12/1991 |
| WO | 9426221 A1 | 11/1994 |
| WO | 9507674 A2 | 3/1995 |
| WO | 9610380 A2 | 4/1996 |
| WO | 9612369 A1 | 4/1996 |
| WO | 9623469 A1 | 8/1996 |
| WO | 9842287 A1 | 10/1998 |
| WO | 9956690 A1 | 11/1999 |
| WO | 0038915 A1 | 7/2000 |
| WO | 0065083 A2 | 11/2000 |
| WO | 0132318 A2 | 5/2001 |
| WO | 0172252 A1 | 10/2001 |
| WO | 2004049995 A1 | 6/2004 |
| WO | 2005115296 A1 | 12/2005 |

OTHER PUBLICATIONS

8819 PCT Search Report for PCT/US02/40229 dated Jun. 23, 2003.

AA597 International Search Report for PCT/US03/21363 dated Dec. 19, 2003.

Depend Regular Absorbency Undergarment Belted, Purchased Oct. 1, 1996.

European Search Report for Case 8819D—Application 10181789.8 dated Mar. 31, 2011.

Iroirozatsugaku/Konica Minolta "Color Digitalization In Each Color Specification System"—no dates provided.

Serenity Pad for Urine Leakage, Purchased Oct. 11, 1993.

"Carefree Teens colored pantyliners, Personal Products, U.S.A., about 1990," Carefree Teens pantyliners for teenagers at the Museum of Menstruation and Women's Health (http://mum.org/crfrteen.htm).

"Multicolored Absorbent Articles: A Brief History," Jeffrey D. Lindsay and Beth A. Lange, Kimberly-Clark Corporation, Neenah, Wisconsin, Published in: IP.com's Prior Art Database, Oct. 10, 2003; Publication ID: IPCOM000019928D.

All Office Actions for U.S. Appl. No. 15/679,618, filed Aug. 17, 2017.

All Office Actions for U.S. Appl. No. 13/974,5511, filed Aug. 23, 2018.

* cited by examiner

ABSORBENT ARTICLE HAVING A PRINTED REGION

FIELD OF THE INVENTION

The present invention is directed to long, asymmetrical absorbent articles having printed regions to facilitate individual placement of the absorbent article.

BACKGROUND OF THE INVENTION

Some commercially-available absorbent articles are extremely long to help manage large volumes of fluid and/or to provide additional coverage for fluid paths depending on the position of the wearer (e.g., lying down). Extra-heavy flow and overnight products can also be asymmetric about their transverse axis, with different geometries and/or fluid management properties associated with the first and second longitudinal ends (e.g., these articles can have a large end and a small end). Due to the length and asymmetry, placement of the article in one's undergarments can be confusing.

Over time, individuals can notice trends of where an absorbent article captures fluid or leaks according to their body type, fluid flow, and typical activities. For example, some individuals may tend to capture fluid or leak towards the front of an absorbent article. Some individuals may discover the opposite. As consumers learn about their needs with the use of a chosen product, they can individualize the placement of the article to best suit their individual fluid management needs. For example, for the consumer that tends to see fluid flow towards the front of the article, they can place the larger end in the front of their undergarment. It would be helpful to consumers to provide a long, asymmetric article with a printed region that does not span the entire length of the article to serve as their personal guide for individual placement. A large portion of commercially-available absorbent articles contain printed regions, but some of the longest and/or asymmetrical products are devoid of printed features. And as discussed above, this represents a long-felt and unmet need. Embodiments of the present invention can address this need.

BRIEF DESCRIPTION OF THE DRAWINGS

The following detailed description of specific embodiments of the present invention can be best understood when read in conjunction with the drawings enclosed herewith.

Figure 1:
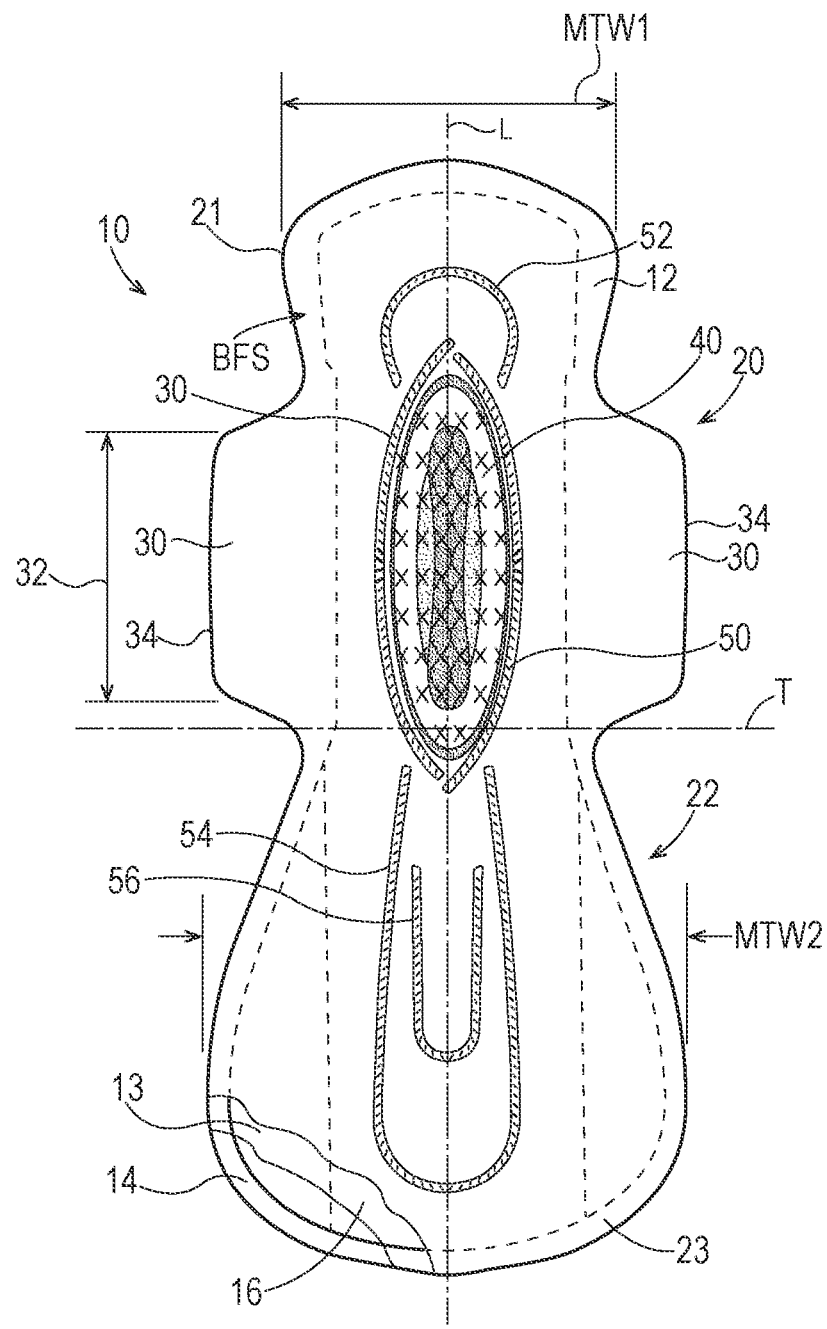
FIG. 1 is a plan view of a body-facing side of a first absorbent article embodiment of the present invention.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As used herein, the term "absorbent article" refers to devices that can capture, absorb and/or contain liquid, and more specifically, refers to devices that are placed against or in proximity to the body of the wearer to absorb and contain the various exudates discharged from the body. A non-limiting list of absorbent articles includes feminine hygiene articles, diapers, incontinence products, and pants/briefs.

As used herein, the term "feminine hygiene article" refers to disposable absorbent articles to be worn by women for menstrual and/or light incontinence control. Feminine hygiene articles are typically held in place adjacent the user's externally-visible genitalia (i.e., the pudendal region) by the user's undergarment. Feminine hygiene articles can be placed into the user's undergarment and affixed via adhesive or other joining means.

FIG. 1 shows a partially cut-away plan view of one absorbent article embodiment of the present invention. Absorbent article 10 includes a topsheet 12, a backsheet 14, and an absorbent core 16 disposed therebetween. Topsheet 12 can be formed from any generally soft, compliant, and porous material which is comfortable against human skin and through which bodily exudates can pass. Exemplary topsheets include nonwovens and apertured polymeric films. Backsheet 14 is generally configured to hinder or prevent bodily exudates from penetrating all the way through the absorbent article and soiling a user's garments or body. The backsheet can be liquid impermeable and be formed from polymer films or film/nonwoven laminates. Backsheets can be vapor permeable while being liquid impermeable to help render the article more breathable. Exemplary vapor permeable materials include microporous films, apertured formed films, and nonwovens. Such materials may include an additive (e.g., wax or surfactant) or treatment to increase their hydrophobicity. Absorbent core 16 can be formed from any of the materials well known to those of ordinary skill in the art. Examples of such materials include, but are not limited to, plies of creped cellulose wadding, fluffed cellulose fibers, wood pulp fibers known as airfelt, a mass or batt of fibers, airlaid webs or fibers, a web of polymeric fibers, and a blend of polymeric fibers. The absorbent core can also comprise high capacity materials such as polyacrylate particles (often referred to as "superabsorbents" and absorbent gelling material (AGM)) and HIPE foams like those disclosed in U.S. Pat. Nos. 5,550,167; 5,387,207; 5,352,711; and 5,331,015.

One or more optional intermediate layers can be employed in the absorbent articles of the present invention. In one configuration, an optional intermediate layer can be disposed between the topsheet and the absorbent core. Such layers are included in many known absorbent article designs and can be referred to as "secondary topsheets," "surge layers," "acquisition layers," "distribution layers," "transport layers," "wicking layers" and the like. With this placement, the optional intermediate layer serves to help rapid acquisition of bodily exudates from the topsheet and movement of the same into the absorbent core, and/or to temporarily hold bodily exudates as a means for managing large loading volumes or fast loading rates. Exemplary surge layers are disclosed in U.S. Pat. Nos. 5,843,063 and 5,879,343. In another configuration, an optional intermediate layer can be disposed between the absorbent core and the backsheet. In this location, an intermediate layer may provide any number of benefits including, for example, structural integrity, flexibility, body shaping, and bodily exudates management.

In some embodiments, absorbent article 10 includes a support layer 13 disposed between absorbent core 16 and backsheet 14. The support layer can help manage bunching and other undesirable wearing effects. As shown in FIG. 1, support layer 13 can extend laterally beyond that of absorbent core 16. Alternatively, the support layer can be laterally coextensive with the absorbent core. The support layer can extend longitudinally to various extents; e.g., substantially the whole length of the article or only a portion of the length of the article. The support layer can comprise a nonwoven, polymer film, paper sheet, plastic scrim, or the like.

The component materials/layers can be combined in a variety of manners to define the finished absorbent article. They can be adhered together with adhesives or thermal bonds, for example. They can also be adhered by mechanical interaction; e.g., by needlepunching or hydroentangling. Some of the component materials/layers can simply reside between adjacent materials/layers without any affixment.

Figure 2:
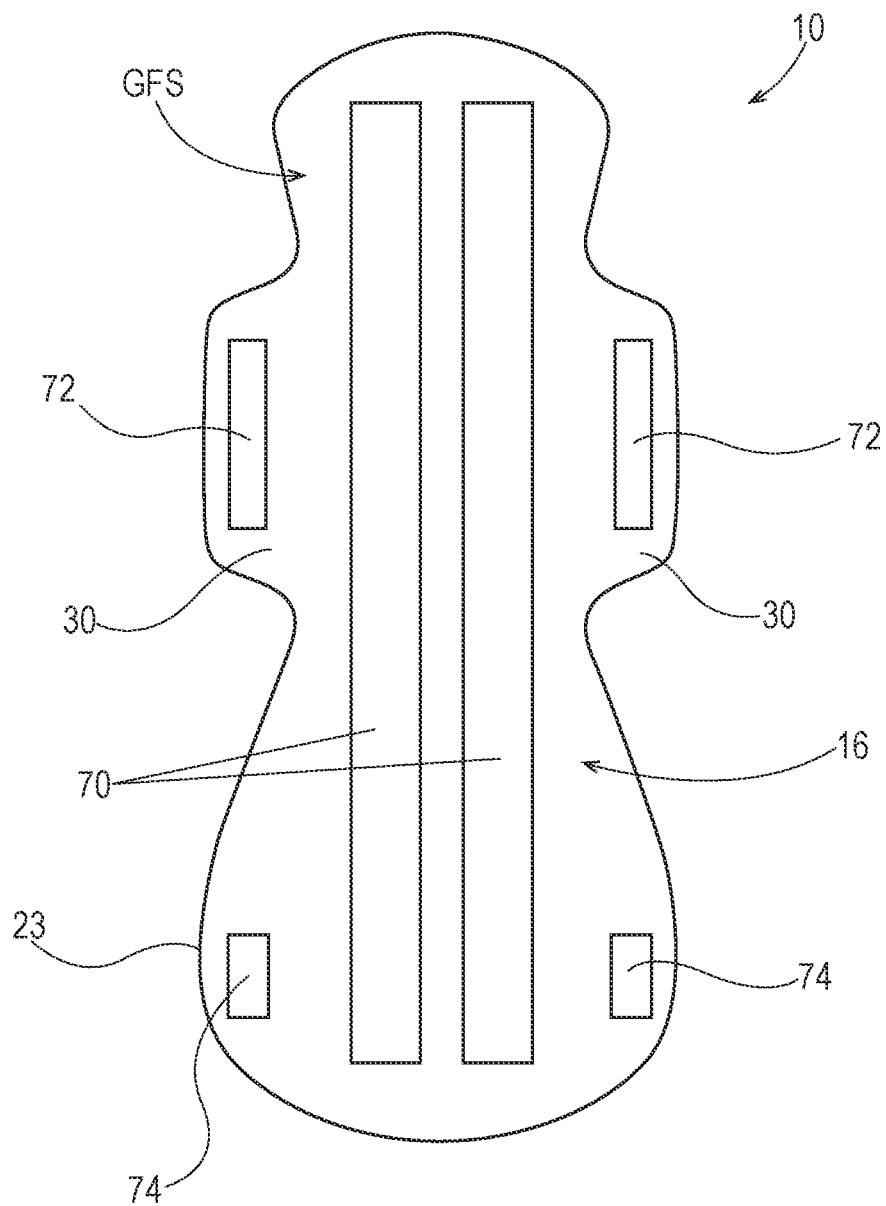
FIG. 2 is a plan view of a garment-facing side of the article shown in FIG. 1.

With reference to FIGS. 1 and 2, the absorbent articles have a body-facing surface (or side) BFS that is in contact with the user's body during use and a garment-facing surface (or side) GFS that is in contact with the user's garment (or undergarment) during use. In general, each component layer of the absorbent article can be said to have a body-facing side and a garment-facing side, the sides being determined by their orientation relative to the in-use orientation of the article.

Absorbent article 10 has a longitudinal centerline L and a transverse centerline T, the centerlines being substantially perpendicular to one another in the plane of the absorbent article when in a flat configuration, as shown in FIG. 1.

Absorbent article 10 includes a first half 20 located on one side of transverse centerline T and a second half 22 located on the opposite side of transverse centerline T. A variety of asymmetries and symmetries are contemplated by the present invention, including along only one or both of the transverse centerline and the longitudinal centerline. The absorbent article in some embodiments is asymmetric about transverse centerline T while being symmetric about longitudinal centerline L, meaning that at least a portion of the first half and the second half are visibly configured differently (e.g., different size, shape, etc.) and/or are configured differently in a manner that is not readily discernible by simply looking at the article (e.g., different exudates management properties or physical properties).

In the exemplary embodiment shown in FIG. 1, absorbent article 10 has a second end 23 associated with second half 22 that includes a maximum transverse width MTW2 that is at least 20% greater than a maximum transverse width MTW1 of a first end 21 associated with first half 20. The maximum transverse differential can also be at least 25%, 30%, 35%, and 40%. Thus, first end 21 and second end 23 are asymmetrical about transverse centerline T. Notably however, absorbent core 16 is substantially symmetrical about transverse centerline T in the embodiment shown in FIG. 1 (e.g., the maximum transverse width dimension for each half is substantially the same).

Exemplary absorbent article 10 has a pair of wings 30 extending laterally from the article. Wings 30 are configured for wrapping around a user's undergarment. Each of wings 30 has a wing length 32 and distal edge 34. Wing length 32 is measured at a point 1 centimeter in from the distal edge along a line that is parallel to longitudinal centerline L. In preferred embodiments, the majority of the wing length is situated on the first half of the absorbent article due to their asymmetrical design (about the transverse centerline). For example, 70%, 80%, 90%, or more than 90% of the wing length can be positioned on the first half of the absorbent article.

As shown in FIG. 1, a printed region 40 is included on the absorbent article. Printed region 40 can be on or associated with at least one of the topsheet, the backsheet, the absorbent core, and the optional intermediate layers. In some embodiments, the absorbent article has a printed region on multiple component layers; for example, a first printed region on a garment-facing side of the topsheet and on a body-facing side of the backsheet. When the printed region exists on multiple component layers, individual aspects of the printed region on the different layers can overlap or be spaced apart from one another. Printing can be done by known processes, such as, for example, gravure printing, offset printing, inkjet printing, V-printing (see, e.g., U.S. Pat. No. 7,731,331) and combinations thereof.

The printed region can include one or more pigments that provide a visual distinction from surrounding areas that are not printed. The color and intensity of the printed region can be measured by reflectance spectrophotometer ASTM standard test methodology. Tristimulus L*, a*, b* values are measured form the body-facing surface of the absorbent article. These L*, a*, b* values are reported in term of the CIE 1976 color coordinate standard. The differences between the printed region and non-printed areas can be determined according to ASTM D244-99 "Standard Test Method for Calculation of Color Differences from Instrumentally Measured Color Coordinates." Intensity of the printed region can be determined by ΔE* calculations between the printed region and non-printed areas, or through a saturation determination (Chromo or C*). In some embodiments, the ΔE* calculation between the printed region and a non-printed area is at least 3.5.

Despite the location of the printed region, it should be visually perceptible when viewing the body-facing side of the article, meaning that a human viewer can visually discern at least some of the printed region with the unaided eye (excepting standard corrective lenses adapted to compensate for near-sightedness, farsightedness, or stigmatism, or other corrected vision) in lighting at least equal to the illumination of a standard 100 watt light bulb at a distance of 1 meter.

The printed region has a printed length and printed area. The printed region can be one solid and continuous design or be made up of multiple design sub-elements. The printed length is an overall length measurement from terminal points of the printed region along a line parallel to longitudinal centerline L. The printed area can be measured by any known techniques, including, for example, imagining the article to capture the visibly discernible printed area and then measuring/calculating the number of pixels associated with the printed area. Pixels can be color-characterized by assigning them RGB or L*a*b* values. And the measurement or calculation of the pixels can be filtered for inclusion by assigned color values. Color characterization can also be used for determining intensity of aspects of the printed area.

Figure 3:
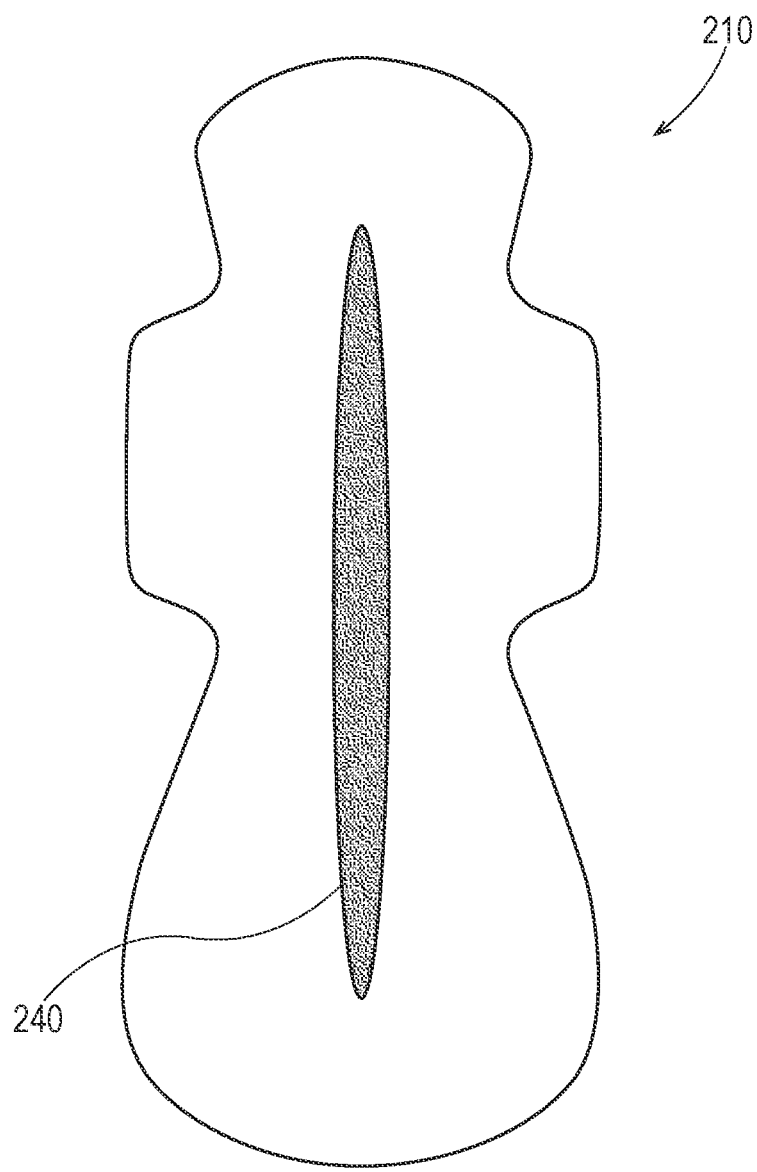
FIG. 3 is a plan view of a body-facing side of a second absorbent article embodiment of the present invention.
Figure 4:
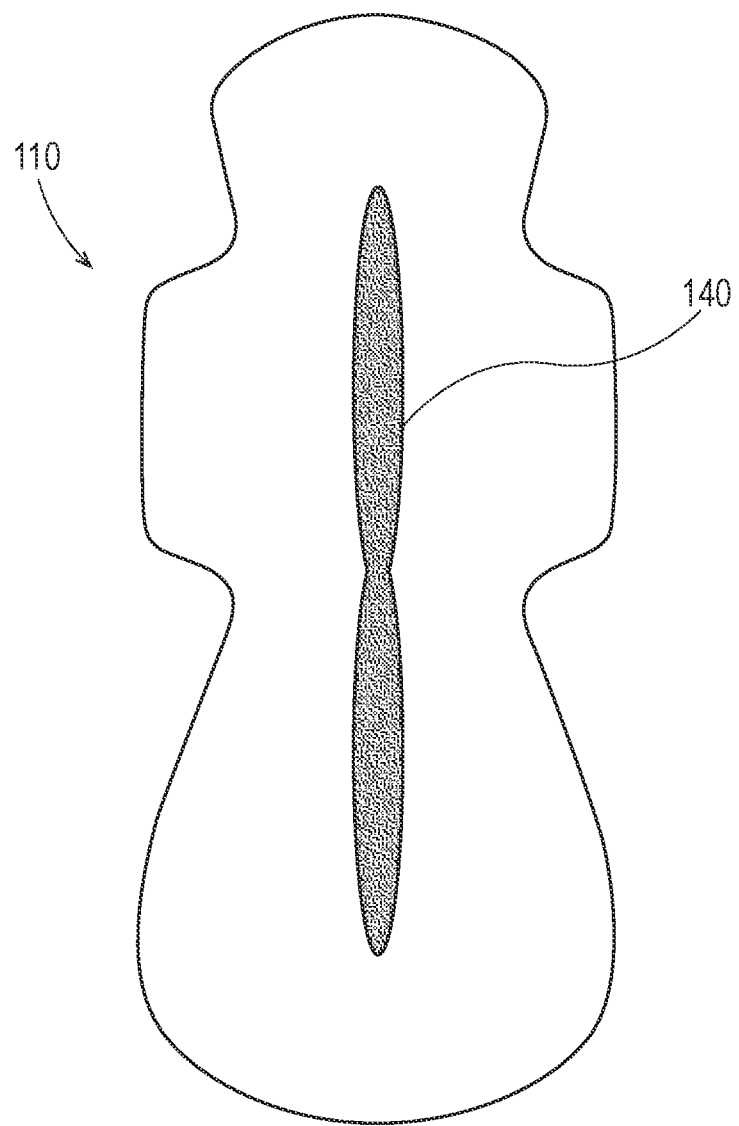
FIG. 4 is a plan view of a body-facing side of a third absorbent article embodiment of the present invention.

More than 50%, 70%, or 90% of the maximum printed length can be positioned on the first half of the absorbent article in some embodiments. And more than 50%, 70%, or 90% of the printed area can be positioned on the first half of the absorbent article. The printed region may not exist at all on the second half of the absorbent article. In other embodiments, the printed region can be substantially centrally located about the transverse centerline, or be skewed towards the second half of the absorbent article. FIGS. 3 and 4 show alternative embodiments, with variations in the geometry and location of the printed region. Absorbent articles 110 and 210 include a printed region 140 and 240, respectively, that exists on both the first half and the second half of the article.

Figure 5:
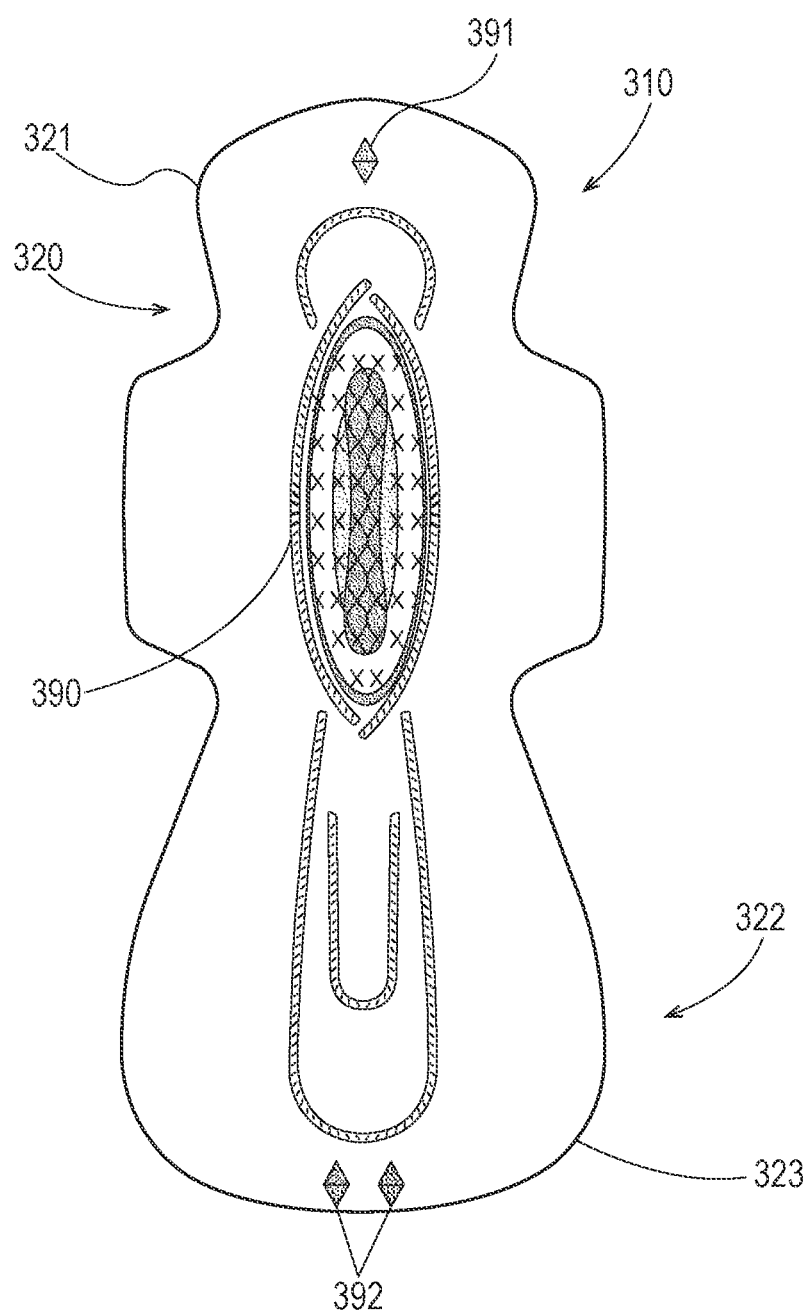
FIG. 5 is a plan view of a body-facing side of a fourth absorbent article embodiment of the present invention.

Referring now to FIG. 5, exemplary article 310 is shown having a printed region comprising three printed elements 390, 391, and 392. Printed element 391 is a single diamond of a first color situated on a first end 321 of article 310. And printed element 392 is defined by two diamonds of a second color situated on a second end 323 of article 310. Collectively, the majority of the printed region exists on first half 320. Thus, the printed region exists in a different manner in the first half 320 versus the second half 322. As discussed in the background section above, consumers may notice trends of where an absorbent article captures fluid or leaks according to their body type, fluid flow, and typical activities. Some individuals may tend to capture fluid or leak towards the front of an absorbent article. For these individuals, they may choose to orient article 310 such that wider end 323 is positioned in the front portion of their undergarment. Some individuals may discover the opposite, wherein they choose to orient article 310 such that wider end 323 is positioned in the rear portion of their undergarment. As consumers learn about their needs with the use of a chosen product, they can individualize the placement of the article to best suit their individual fluid management needs via characteristics of the printed region.

The description thus far has focused on printing on a component material (e.g, a topsheet) to provide a visibly-distinct area of the absorbent article. Alternative methods are also contemplated by the present invention. For example, fibers, particles or other raw materials from which component materials/layers are made can include colorants (e.g., pigments, dyes). Component materials may be manipulated further to create a design leveraging the colorants in the raw materials. For example, the component material may be embossed, needlepunched, or hydroentangled to create a design via the colorants. Alternatively, the design may be manifested simply by how the raw materials containing a colorant are incorporated into the component material without further manipulation. In some embodiments, the entire component material may appear to be colored (non-white), wherein the shape of the component material itself provides the visibly-distinct design.

Absorbent articles of the present invention may optionally employ a variety of other surface and/or deeper features to help manage acquisition and containment of bodily exudates. By way of example and with reference to FIG. 1, absorbent article 10 employs a series of embossed channels, including first half central channels 50 and end channels 52, 54, and 56. As shown in FIG. 1, printed region 40 of exemplary absorbent article 10 is at least partially framed laterally by channels 50 and longitudinally by channels 52, 54, and 56. Other configurations of the printed region in relation to channels or other features are contemplated by the present invention.

As noted in the background section, exemplary embodiments of the present invention are directed to long, asymmetrical absorbent articles. Referring again to FIG. 1, preferred absorbent articles have an overall length 60 (as measured on a line parallel to the longitudinal centerline) of at least 330, 340, 350, 360, 370, 380, 390, or 400 millimeters.

Garment-facing surface GFS is shown in FIG. 2. Multiple pressure-sensitive adhesive zones are shown on exemplary absorbent article 10. Two, spaced apart central adhesive zones 70 are shown running along a substantial length of article 10. Adhesive zones 72 are employed on wings 30 to help secure the wings to the underside of one's undergarment. Exemplary absorbent article 10 includes another pair of adhesive zones 74 on distal areas of widened end 23. Depending on the dimensions of the undergarment, adhesive zones 74 can be adhered to a body-facing surface of one's undergarment or the underside of the same; i.e., the distal areas of end 23 may optionally be used as a second pair of wings. The skilled artisan should appreciate that other temporary attachment means may be employed to secure the absorbent article to one's undergarment.

Absorbent articles of the present invention can be folded and manipulated in numerous ways for packaging and portability. Absorbent article 10 is partially folded in FIG. 6, with wings 30 and portions of second half 22 and second end 23 folded laterally inward. The absorbent article can then optionally be folded lengthwise along one or more (e.g., three) transverse folding lines to render the overall size more manageable for discreetly carrying replacement articles around. Adhesive zones 72 and 74 are covered with a protection sheet 73. A portion of printed region 40 is visible and can act as a placement guide for consumers. That is, a consumer can utilize adhesive zones 70 (shown in FIG. 2) to place article 10 in their undergarment before removing protective sheet 73 from adhesive zones 72 and 74. They are able to do this, at least partly, by utilizing the visible portion of printed region 40. The vast majority of commercially-available articles that have portions (e.g., wings) folded laterally inward only have one portion done so. Asymmetric articles that have enlarged ends in addition to wings, such as exemplary article 10, can have two separate portions folded laterally inwardly. Consumers may be confused about placement into their undergarment when confronted with multiple inwardly folded sections (particularly when the sections are spaced apart along the length of the article). The skilled artisan will appreciate that adhesive zone 70 can also have a protective sheet and a wrapping film or layer can be used alternatively or in addition to the same for individually wrapping absorbent article 10.

Figure 6:
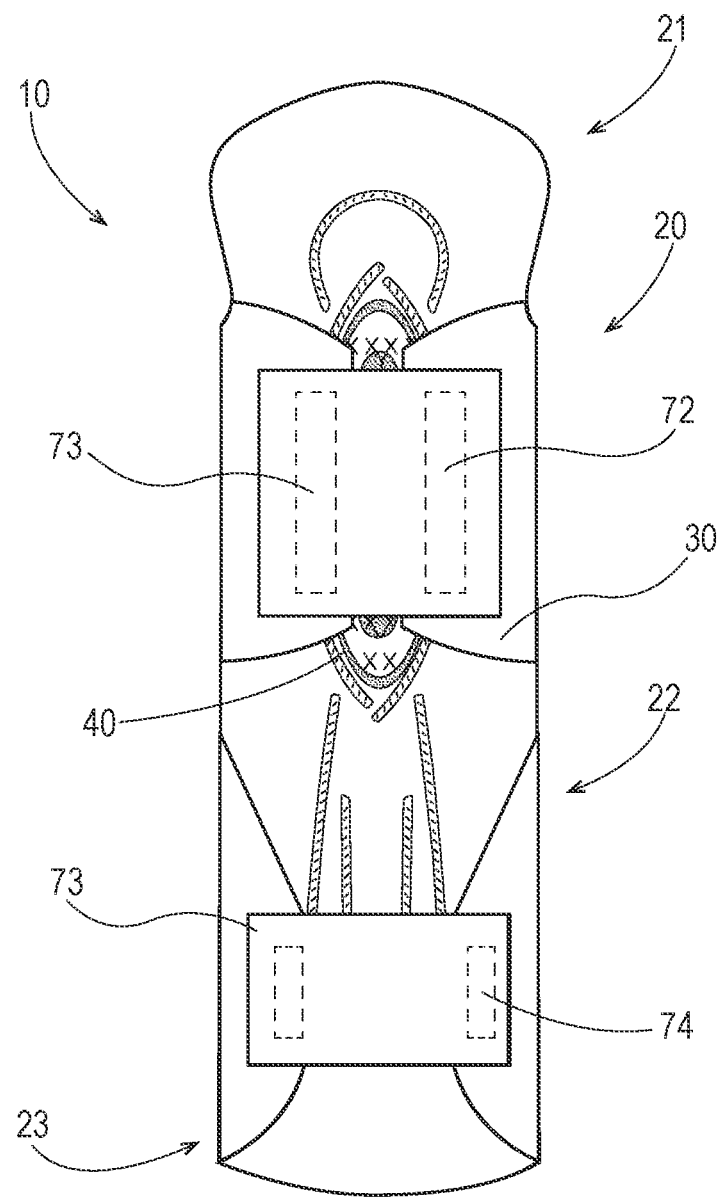
FIG. 6 is a plan view of an absorbent article of the present invention, wherein the article is in a partially folded configuration prior to use.

The present invention contemplates alternative configurations to that shown in FIG. 6. For example, rather than having two separate protection sheets, a single, long sheet can extend sufficiently to cover both adhesive zones 72 and 74. In this arrangement, a portion of the printed zone can be visible towards end 21. Furthermore, the protection sheet(s) can be made such that a printed region can be visible through the protection sheet(s). For example, the protection sheet may have window or discontinuity area, or be made from a material that is transparent or translucent enough to see an underlying printed region so that a consumer can use the printed region for proper placement prior to exposing adhesive zones 72 and 74. There can also be two different printed zones (or two portions of a single printed zone) that exist under each of the inwardly folded portions (wings 30 and second half 22/second end 23), wherein the features of the printing can be differentiated from one another to provide guidance on placement of the article into one's undergarment. Such differentiation can be, for example, color, color intensity, geometrical shape, text, or other communicative indicia.

In addition to the asymmetries discussed above, the absorbent articles of the present invention can have varying calipers. This can be achieved by incorporating a different number of component materials/layers in one part of the article versus another part, and/or by varying the caliper of individual component materials/layers. For example, a stacked absorbent core can be utilized with the area or "footprint" of the two core layers being different from one another. The difference in caliper can be as much as 3, 4, 5, 6, 7, 8, or 9 millimeters. The absorbent article can have one portion having a first caliper and another portion having a second caliper that is different (smaller or greater) than the first caliper, wherein the printed region is biased (positioning, intensity, amount of ink/pigment, area, length, geometrical focusing) towards the first or second caliper. Again, this can help a consumer in their chosen placement of a variable thickness article to best suit their individual needs.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a longitudinal centerline and a transverse centerline generally perpendicular to the longitudinal centerline, the absorbent article further comprising:
   a topsheet;
   a backsheet;
   an absorbent core disposed between the topsheet and the backsheet;
   a first half of the article located on one side of the transverse centerline and a second half of the article located on the opposite side of the transverse centerline;
   a pair of wings extending laterally from the article, each of the wings configured for wrapping around a portion of a user's undergarment and comprising a wing length, wherein 70% or more of the wing length is positioned on the first half;
   a first end associated with the first half;
   a second end associated with the second half, wherein the second end comprises a maximum width that is at least 20% greater than that of the first end so that the first end and the second end are asymmetrical about the transverse centerline; and
   a printed region on at least one of the topsheet, the backsheet, and the absorbent core, the printed region intersecting the longitudinal centerline and having a length which is oriented generally parallel thereto, wherein the printed region exists in the first half, and wherein the printed region is partially framed by a pair of embossed channels which extend generally in a transverse direction and are generally concave to the transverse centerline.

2. The absorbent article of claim 1, wherein each of the pair of embossed channels are disposed in the second half.

3. The absorbent article of claim 1, wherein one of the pair of embossed channels is disposed in the second half, and one of the pair of embossed channels is disposed in the first half.

4. The absorbent article of claim 1, further comprising an intermediate layer disposed between the topsheet and the absorbent core.

5. The absorbent article of claim 4, wherein the intermediate layer comprises a nonwoven material.

6. The absorbent article of claim 1, comprising a support layer disposed between the absorbent core and the backsheet.

7. The absorbent article of claim 6, wherein the support layer comprises a nonwoven material.

8. The article of claim 6, wherein the support layer extends laterally outward of the absorbent core in the second end.

9. The article of claim 1, wherein the printed region does not exist in the second half.

10. The article of claim 1, wherein more than 90% of the wing length is positioned on the first half.

11. The article of claim 1, wherein the printed region has a printed area and wherein more than 70% of the printed area is positioned on the first half.

12. The article of claim 1, wherein the printed region comprises a printed length and wherein more than 70% of the printed length is positioned on the first half.

13. The article of claim 1, wherein the article has an overall length of at least 330 millimeters.

14. An absorbent article comprising a longitudinal centerline and a transverse centerline generally perpendicular to the longitudinal centerline, the absorbent article further comprising:
- a topsheet;
- a backsheet;
- an absorbent core disposed between the topsheet and the backsheet;
- a first half of the article located on one side of the transverse centerline and a second half of the article located on the opposite side of the transverse centerline;
- a pair of wings extending laterally from the article, each of the wings configured for wrapping around a portion of a user's undergarment and comprising a wing length, wherein 70% or more of the wing length is positioned on the first half;
- a first end associated with the first half;
- a second end associated with the second half, wherein the second end comprises a maximum width that is at least 20% greater than that of the first end so that the first end and the second end are asymmetrical about the transverse centerline; and
- a printed region on at least one of the topsheet, the backsheet, and the absorbent core, the printed region intersecting the longitudinal centerline and having a length which is oriented generally parallel thereto, wherein the printed region exists in the first half, and wherein the printed region is partially framed by a pair of embossed channels which extend generally in a longitudinal direction and are generally concave to the longitudinal centerline.

* * * * *